Figure 1:
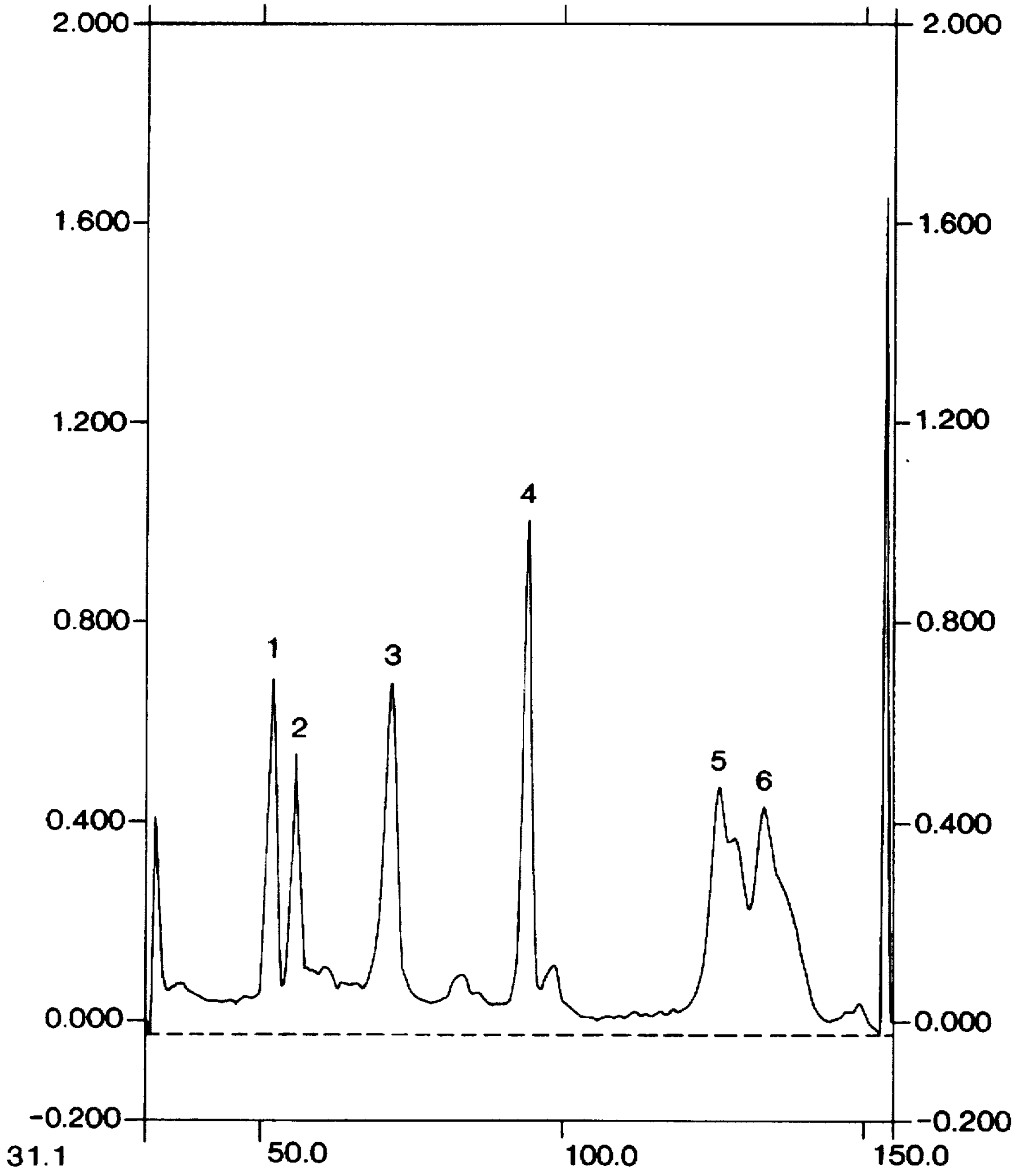

US005750115A

United States Patent [19]

Van Den Bosch

[11] Patent Number: 5,750,115

[45] Date of Patent: May 12, 1998

[54] ***ESCHERICHIA COLI* VACCINE**

[75] Inventor: Johannes Franciscus Van Den Bosch, Boxmeer, Netherlands

[73] Assignee: Akzo Nobel N. V., Arnhem, Netherlands

[21] Appl. No.: 420,454

[22] Filed: Apr. 10, 1995

Related U.S. Application Data

[63] Continuation of Ser. No. 967,912, Oct. 25, 1992, abandoned, which is a continuation of Ser. No. 711,128, Jun. 6, 1991, abandoned, which is a continuation of Ser. No. 562,527, Aug. 3, 1990, abandoned.

[30] Foreign Application Priority Data

Aug. 3, 1989 [EP] European Pat. Off. .............. 89202110

[51] Int. Cl.$^6$ ............................ A61K 39/108; C12N 1/20

[52] U.S. Cl. .................................... 424/241.1; 424/185.1; 424/197.11; 424/190.1; 424/257.1; 435/252.1; 435/252.8

[58] Field of Search ............................. 424/185.1, 190.1, 424/197.11, 241.1, 257.1; 435/252.1, 252.8

[56] References Cited

U.S. PATENT DOCUMENTS 4,772,464 9/1988 Rutherford ................................ 424/87
4,886,748 12/1989 Asaka ..................................... 435/69.7

FOREIGN PATENT DOCUMENTS 0135819 8/1983 Japan .
135819 8/1983 Japan .

OTHER PUBLICATIONS

H.T. Campbell et al., "Immunization with Flagella or Anti-Flagella Sera Protects Mice Against Salmonella-enteritidis", Absts. Ann. Meeting Am. Soc. Microbiol. 72: 101, Abst. M131, Apr. 1972.

M. Tanaka et al., "Production, Characterization, and Protective Effect of Monoclonal Antibodies to *Clostridium chauvoei* Flagella", Infect. Immun. 55(8) 1779–1783, Aug. 1987.

G. Resnick et al., "Improved Protection Against Cholera in Adult Rabbits with a Combined Flagellar-Toxoid Vaccine", Infect. Immun. 30(2) 375–380.

I.A. Holder et al., "Experimental Studies of the Pathogenesis of Infections Due to *Pseudomonas aeruginosa* : Immunization Using Divalent Flagella Preparations", J. Trauma, 26(2), 118–122, Feb. 1986.

Analytical Chemistry, vol. 28, pp. 350–356, (1956).

Journal of Bacteriology, vol. 168, No. 3, pp. 1479–1485 (1986).

Chromatographia, Jannsen et al., vol. 22, pp. 345–358 (1986).

Journal of General Microbiology, vol. 101, pp. 112–130 (1977).

The Journal of Biological Chemistry, vol. 73, No. 2, pp. 627–650, (1927).

Whitfield et al (1988) J. Gen. Microbiol. 134, 1747–1753.

Kuwajima et al (1986) J. Bacteriol. 168, 1479–1483.

Wei et al. (1985) J. Mol. Biol. 186, 791–803.

Newton et al (1989) Science 244, 70–72.

Gel Filtration: Theory and Practice, Rahms i Lund, Sweden (1984) pp. 4, 16–19 & 30–35.

Hackett et al., Dialog Abstract from J. Infect. Disease 157, 78–84 (1988).

Kondoh et al, Dialog Abstract from Biochem. Biophys. Acta. 336, 117–39 (1974).

Kramer, Dialog Abstract from Inagural Dissertation (1983).

Sherman et al (1988) J. Clin. Microbiol. 26(7), 1367–1372.

*Primary Examiner*—Rebecca E. Prouty
*Attorney, Agent, or Firm*—William M. Blackstone; Mary E. Gormley

[57] ABSTRACT

According to the present invention it has been found that a novel *E. coli* toxin or an immunogenic fragment thereof can be used in the preparation of vaccines for warm-blooded animals, and in particular for birds. Said toxin is found to be associated in flagellar structures attached to the bacteria, and these flagella or the free toxins can, after inactivation be used to immunize animals against *E. coli* infections.

7 Claims, 3 Drawing Sheets

*ESCHERICHIA COLI* VACCINE

This is a continuation of U.S. Ser. No. 07/967,912, filed Oct. 28, 1992, now abandoned, which is a file wrapper continuation of U.S. Ser. No. 07/711,128, filed Jun. 6, 1991, now abandoned, which is a file wrapper continuation of U.S. Ser. No. 07/562,527, filed Aug. 3, 1990, now abandoned.

The invention is concerned with a vaccine for the protection of individuals against *Escherichia coli* (*E. coli*) infection, a toxin for use in such a vaccine and a method for the purification of such a toxin.

*E. coli* is a widespread bacterium that colonizes the digestive tract of most animals. In general, such a colonization goes without serious negative effects—in most cases the bacterium even contributes to processes which are favourable to its host. However, occasionally *E. coli* causes serious diseases particularly in young animals. This can also occur in birds and in the commercial poultry breeding such an infection can become epidemic, leading to serious weakening or even massive mortality among the young birds.

Naturally, it has been attempted to have such *E. coli* infections amoung poultry in hand by vaccination programs. To this end mature chickens have been vaccinated with bacterins—inactivated *E. coli* bacteria (Avian Diseases 29(4), 1108–17 (1985)). A disadvantage of bacterin vaccines is the concommitant serious side reactions. Furthermore, bacterin vaccination results primarily in antibodies against lipopolysaccharides which are only specific for a certain *E. coli* O serotype and hence are not protective against other *E. coli* serotypes.

For the combatment of *E. coli* infections also frequently use is made of vaccines based on pili obtained from these bacteria. However, these vaccines only lead to a limited protection of not more than about 80% of the vaccinated individuals. For this reason *E. coli* vaccines often contain as a component yet another virulence factor: inactivated toxin of *E. coli.*

Many types of *E. coli* contain flagella, having a function in locomotion. For *E. coli* flagella have not been considered as a factor of virulence, and hence have not been included in *E. coli* vaccines.

According to the present invention, it has been found that the flagella of *E. coli* are associated with a profound toxic activity towards Vero cells, which was hitherto not recognized, and that these flagellar toxins are a significant factor of virulence.

In view of this finding vaccines have been prepared derived from flagella of *E. coli*. According to the present invention whole flagella of *E. coli* can be used, as well as substructures thereof composing said flagella, e.g. flagellins or fragments or aggregates of the flagellins which protect individuals vaccinated therewith against *E. coli* infections.

In experiments with a large number of *E. coli* strains, isolated mainly from chicken but also from other animals and humans, flagella were found to be associated with toxicity against Vero cells; this toxic activity was found to be neutralized by antibodies against the flagella. It further turned out that the toxicity of the flagella of all *E. coli* strains studied could be neutralized by a single antiserum raised against flagella of one of the strains.

In view of this finding it is anticipated that vaccination with flagella obtained from a single *E. coli* strain will provide protection against infection with all flagella bearing *E. coli* strains.

In view of the above considerations the vaccine according to the invention is based on a novel class of toxins found in *E. coli* and which are characterized in that they are of protein nature, are found associated in and/or with flagella, and have a molecular weight of between 30–100 kD measured in SDS-PAGE, do not possess bound carbohydrate residues, are toxic to Vero cells and to day-old chicks and keep this toxicity even on heating for 1 hour at 100° C.

The combined characteristics distinguish these novel toxins from the *E. coli* toxins known in the art.

The above-described toxins are found among a great number of *E. coli* strains and are named here flagellar toxins (FT) because of their striking occurence in flagellar structures. These flagella generally are significantly larger than normal fimbriae (which typically are about 7 nm in diameter and up till about 1 μm long), and are up to 25 nm thick and 7 μm long.

One member of the class of toxins according to the present invention was isolated from the chicken *E. coli* strain CH7 (015:K14:H10) according to the procedure outlined in Example 1. This CH7-FT can be isolated in several forms: either associated as the native flagella of type H10, or as the free toxin, or re-associated to small needle-like filaments obtained from the free toxin. Typical characteristics of this CH7-FT on top of the afore-mentioned general characteristics are a subunit molecular weight of about 47 kD as determined by SDS-PAGE, an iso-electric pH of about 4.8 and the partial amino-terminal amino acid sequence: Ala-Gln-Val-Ile-Asn-Thr-Asn-Ser-Leu-Ser-Leu-(?)-Thr-Gln. (The characterization of CH7-FT is described in Example 2).

Antiserum raised against this CH7-FT was found to cross-react with FT of all other *E. coli* strains tested (Example 3). Accordingly, such an antiserum against CH7-FT can be used to characterize all other FT's according to the present invention. Furthermore, monoclonal antibodies were either specific or cross-reactive with FT of all other *E. coli* strains tested.

The present invention also comprises vaccines with immunizing activity against *E. coli* infection, wherein the active ingredient is an inactivated toxin according to the present invention.

Such a vaccine suitably contains said toxic flagella as these flagella can readily be obtained by culturing *E. coli* bacteria under conditions promoting the formation of flagella, and separating the flagella or the cell free supernatant from the bacteria. The FT can be further purified by removal of low molecular weight components of the supernatant using ultrafiltration and/or molecular sieve chromatography.

During this purification process the fraction enriched in FT can be monitored by its reactivity with the monoclonal antibodies raised against CH7-FT.

A vaccine according to the invention may also comprise a fragment of FT which protects individuals vaccinated therewith against *E. coli* infection.

A FT to be incorporated into a vaccine according to the invention can be obtained by chemical synthesis, purification from *E. coli* cell culture or by recombinant DNA technology.

In the latter case nucleic acid sequences encoding above-mentioned protein or fragments thereof can for example be identified by screening a genomic *E. coli* DNA bank for individual clones comprising said sequences, e.g. by using a specific reaction with polyclonal or monoclonal antibodies elicited against FT. The nucleic acid sequences can be ligated to various expression effecting DNA sequences, resulting in a so called recombinant nucleic acid molecule which can be used for the transformation of a suitable host. Such hybrid DNA molecules can for example be derived from plasmids, phages or from nucleic acid sequences present in viruses. The host cell can be of prokaryotic origin, e.g. bacteria or eukaryotic origin such as mammalian cells. The transformed host cells can be used to produce the FT whereafter said protein can be isolated and subsequently incorporated into a vaccine according to the invention.

In another embodiment a live vector vaccine can be prepared comprising non-pathogenic micro-organisms, e.g. viruses or bacteria containing the gene encoding the FT.

Apart from FT a vaccine according to the present invention may also contain an aqueous medium or a water containing suspension, and/or other constituents e.g. in order to increase the activity and/or the shelf life. These constituents may be salts, agents to inactivate the toxic activity of FT while maintaining its immunogenic properties (e.g. formalin), pH buffers, emulsifiers and adjuvants to improve the immune response (e.g. mineral oils, muramyl dipeptide, aluminium hydroxide, saponin, polyanions and amphiphatic substances).

The vaccine is useful in immunizing warmblooded animals (including man) against *E. coli* infections and in particular can be used to combat *E. coli* infections in birds.

To this end the vaccine preferably is administered parenterally, for example subcutaneously or intramuscularly. The vaccine may be administered in this manner both for the active immunization of the vaccinated birds and to laying birds for the passive immunization of the offspring thereof. In immunized laying birds, the antibodies raised in them will, of course, be introduced into the yolks of their eggs and therefore subsequently in the hatched chicks.

Both the composition of the vaccine and the vaccination system can be varied and depend on the type of animal to be protected, the age and the weight of the animal, the desired duration of the protection, the method of administration and on the question of whether active immunization or passive immunization by means of maternal antibodies is desired. The optimally effective quantity of the active component in the vaccine is approximately 10–100 μg per dose for parenteral vaccination of poultry. The vaccine may be combined with other relevant vaccines.

EXAMPLE 1

Isolation of Flagellar Toxin of *E. coli* strain CH7

A. Preparation of Flagellar Toxin

*E. coli* strain CH7 (015:K14:H10) was cultured overnight in a Biostat E fermentor (Braun) in 12 l Trypticase Soy Broth (B.B.L.) at a $pO_2$ setting of 14% and variable stirring from 100–500 rpm. The culture was concentrated to approx. 1 l in a Pellicon filter system (Millipore) with a HVLP filter. Bacteria were centrifuged for 30 minutes at 10,000 rpm (GSA rotor, Sorvall), the supernatant filtered through a 0.45 μm filter and added to the HVLP filtrate.

The filtrate was concentrated to approx. 1 l and washed with 3 times 1 l 0.2 mol/l Tris HCl buffer using a PTTK filter.

The PTTK concentrate was repetitively eluted in portions of about 110–160 ml over a sepharose 4B-Cl column (Pharmacia, Uppsala Sweden) with a height of 10 cm and an area of 154 $cm^2$ (Amicon model P140×250) equilibrated in phosphate buffer 50 mmol/l pH 7.2 with 0.1% $NaN_3$ as a preservative (PB). The column was eluted with PB until the baseline of the recorder was zero again.

The fractions of the first peak, containing the high molecular weight molecules were pooled, and concentrated on an YM-100 ultrafiltration filter (Ø 62 mm Amicon, with Amicon UF model 202) until the protein concentration was about 2–3 mg/ml. The concentrate was dialysed twice against 5 l Tris HCl buffer 20 mmol/l pH 7.5 with 0.1% $NaN_3$ as preservative.

B. Preparation of Free Toxin

The concentrate was preparatively electrophoreted by the method of Laemmli (Nature 227, 680–4; 1970). It was 1:1.67 diluted in sample buffer composed of 20 ml glycerol, 20 ml Tris-HCl buffer 0.5 mol/l pH 6.8, 20 ml 10% SDS, 5 ml 2-mercaptoethanol (ME) and 2 ml 0.05% bromophenol blue.

Then it was boiled for about 5 minutes in water, cooled off and electrophoreted on a 12% (acrylamide:bis 30:0.8) preparative polyacrylamide slab gel of 16×0.6 cm. Typically sample loads were about 15–23 mg protein per gel (7.5 ml concentrate and 5.0 ml sample bufer). The electrophoreses was performed on a Protean cell model 1423 (Bio-Rad, Richmond USA) or a model SE600 (Hoefer, San Francisco, USA). After the front was eluted from the gel the electrophoresis was continued for another hour at 200 V. The gel was cut in slices of about 1.5–2 mm.

The proteins were eluted in 10 ml 0.89% sodiumchloride solution+0.1% $NaN_3$, for three hours at room-temperature and overnight at 4° C. under continuous agitation. The slices were removed and the solutions were filtrated over a 0.45μfilter. The fractions containing pure toxin subunits were pooled, and stored at −20° C.

The protein content in the samples was measured by a modified Folin-Ciocalteu assay (J. Biol. Chem. 73, 627; 1927), polysaccharide was measured with use of the phenol-sulphuric acid assay according to Dubois (Anal. Chem. 28, 350–6; 1956).

EXAMPLE 2

Characterization of Toxin of *E. coli* strain CH7

A. Letality for One Day Old Chickens

In a first experiment 0.2 and 0.5 ml of various *E. coli* toxin preparations were injected IP into one-day-old SPF broiler chickens (GVP, Doorn). In a second experiment 0.5 ml of toxin preparations were injected IV into broilers of 3 weeks old. Deaths were recorded for 7 days after injection.

Results

As shown in Table 1, toxin preparations from both chicken *E. coli* strains CH2 and CH7 were lethal for one-day-old chickens after IP injection. For strain CH7 both supernatant as well as lysate were toxic, whereas for strain CH2 especially the lysate was toxic.

TABLE 1

Letality for one-day-old chickens: IP injection of supernatant or lysate from *E. coli* strains.

| Preparation injected* | Dosis (ml) | Dead chickens/total injected on day 1 | 4 | 7 |
|---|---|---|---|---|
| Sterile TSB | 0.5 | | | 1/10 |
| ZF24 sup | 0.2 | | | 1/10 |
| sup | 0.5 | | | 1/10 |
| lys | 0.2 | | | 1/10 |
| lys | 0.5 | | | 1/10 |
| CH2 sup | 0.2 | | 1/10 | 1/10 |
| sup | 0.5 | | 1/10 | 1/10 |
| lys | 0.2 | 9/10 | 9/10 | 9/10 |
| lys | 0.5 | 6/10 | 7/10 | 8/10 |
| CH7 sup | 0.2 | 2/10 | 4/10 | 5/10 |
| sup | 0.5 | 4/10 | 5/10 | 5/10 |
| lys | 0.2 | 4/10 | 4/10 | 4/10 |
| lys | 0.5 | 7/10 | 7/10 | 7/10 |

*Strains CH2 and CH7 are chicken *E. coli* isolates; Strain ZF24 is an avirulent *E. coli* isolate of human feces.

IV injection of similar preparations into 3 weeks old chickens had no effect at all (data not shown).

B. Vero Test

Vero cells were grown at 37° C. in a 5% $CO_2$ atmosphere in medium 6 (per liter containing 85 ml MEM Eagle, 100 ml tryptose phosphate broth, 50 ml 4.4% $NaHCO_3$) supplemented with 5% Fetal Calf Serum (FCS) and 200 U/ml penicillin and 200 µg/ml streptomycin, and after filter sterilisation supplemented with 2 µg/ml fungizone. After trypsinisation the cells were seeded into 96-wells flatbottom polystyrene culture plates (Greiner) with 200 µl per well of complete medium 6 containing $2\times10_5$ cells per ml. After overnight incubation monolayers are established. The medium was discarded and replaced by 200 µl per well of medium 6 without FCS but supplemented with 10 µg/ml xanthine (3-isobutyl-1-methyl-xanthine; Sigma). Subsequently, 20 µl per well of (serial dilutions of) toxin preparations were added. The cytopathological effect (CPE) was recorded after 5 days incubation.

Screening of strains for toxin production was performed firstly by adding 20 µl per well of undiluted and 1:2 diluted supernatants. Secondly, strains from which the supernatants were negative in the Vero test, were tested for intracellular toxin production by adding 50 µl per well of undiluted and 1:2 diluted bacterial lysates.

Results

Initially, the strains listed in Table 2 were tested for toxin production. Some strains excreted toxin in the supernatant whereas with other strains the toxin was intracellular and/or only detectable after ultrasonic disruption of the bacterial cells. The cytopathological effect was rounding and shrinking of the Vero cells, whereas the monolayer stayed intact in most cases.

TABLE 2

Vero cell toxicity of various *E. coli* strains

| Strain* | Serotype | toxin titer** supernatant | in lysate |
|---|---|---|---|
| JA221 | — | — | — |
| ZF24 | 023:K?:H— | — | — |
| CH1 | 078:K80 | — | — |
| CH2 | 078:K80:H4 | — | 8 |
| CH3 | 045:K—:H9 | 32 | 64 |
| CH4 | 02:K1:H— | — | 8 |
| CH5 | 02:K1:H5 | 32 | 512 |
| CH6 | 01:K1:H— | — | 4 |
| CH7 | 015:K14:H10 | 128 | 1,024 |
| CH8 | 0115:K? | — | 16 |
| CH13 | 035:K— | 32 | |

*JA221 is an *E. Coli* K-12 strain, ZF24 see Table 1; CH strains are chicken isolates

**toxin titer is defined as the reciprocal of the last dilution giving a toxic effect C. Stability of the Toxin Preliminary characterisation of the identified toxin was performed by testing the sensitivity of toxin preparations for various treatments. pH sensitivity was tested by adjusting toxin to pH 3 to 10 and neutralisation after overnight incubation at room temperature, prior to toxicity testing.

For heat sensitivity testing toxin preparations were heated at various temperatures. The effect of SDS and ME was tested by heating toxin in the presence of 1% SDS and of 1% SDS with 2.5% ME, and subsequent dialysing against saline. For testing the sensitivity for ureum, 6M ureum was added to toxin preparations for 1 hour and dialysed against saline.

Formalin sensitivity was tested by the addition of various concentrations of formalin, incubation overnight at various temperatures, and dialysing prior to toxicity testing in the Vero cell assay. The sensitivity to trypsin was tested by the addition of 100 µg/ml trypsin (bovine pancreas; Millipore), incubation at 37° C. for 4 hours, and subsequent addition of 150 µg/ml trypsin inhibitor (soybean; Sigma) for 30 min. at 37° C. prior to toxicity testing.

Results Since exact chicken toxin titer determinations in the Vero cell toxicity assay are not very reproducible due to variations in the condition of the Vero cells on different days, results are presented here only as examples of typical experiments.

Treatment of CH5 and CH7 supernatant at pH 3 up to and including 10 did not affect the toxicity, the toxin titers were invariable 32–64 and 128–256 respectively.

The heat sensitivity and the sensitivity to SDS or SDS+ME treatment is shown in Table 3.

TABLE 3

Effect on chicken *E. coli* toxin titers of heating toxin preparations in the absence and presence of SDS or SDS + ME

| Treatment | CH2 lys. | CH5 sup. | CH7 sup. |
|---|---|---|---|
| control | 8 | 32 | 128 |
| 80° C. (1 h) | 4 | 8 | 64 |
| 100° C. (1 h) | 4 | 8 | 16 |
| 120° C. (20 min.) | 0 | 0 | 0 |
| 65° C. (10 min.) | | 16 | 64 |
| SDS, 65° C. (10 min.) | | 32 | 64 |
| SDS + ME, 65° C. (10 min.) | | 32 | 64 |
| 100° C. (10 min.) | | 8 | 64 |
| SDS, 100° C. (10 min.) | | 32 | 128 |
| SDS + ME, 100° C. (10 min.) | | 16 | 128 |

Although the toxicity of CH2 lysate (lys.) and of CH5 and CH7 supernatants (sup.) was somewhat decreased after prolonged exposure to higher temperatures and abolished completely after heating at 120° C., the toxin has to be considered as relatively heat-stable. Heating for 10 min. in the presence of SDS or even SDS+ME had no effect on the toxicity of CH5 and CH7 supernatants.

Treatment of CH2 lysate and CH5 and CH7 supernatants with 6M ureum had no effect at all on the respective VT titers.

As shown in Table 4, the toxicity of CH7 supernatant is inactivated by formalin at room temperature and at 37° C.

The toxicity of both CH5 and CH7 supernatants was abolished completely after treatment with trypsin, whereas sham treatment and treatment with trypsin inhibitor alone had no effect at all on toxicity.

TABLE 4

Inactivation of CH7 supernatant toxicity by incubation overnight with various concentrations of formalin

| Formalin concentration | Toxin titer after incubation at | |
|---|---|---|
| (%) | room temp. | 37° C. |
| 0 | 64 | 64 |
| 0.2 | 32 | 16 |
| 0.5 | 16 | 4 |
| 1.0 | 8 | 2 |
| 2.0 | 1 | 0 |

D. Molecular Weight Determination

The molecular weight of the toxin of strain CH7 was determined by analytical gelelectrophoresis in 12% gels (acrylamide:bis=30:0.8) by the method of Laemmli by comparison with standards.

Gels were stained with coomassie-brilliant blue (CBB). Scans were made using a gelscanner model CS-930 and recorder DR-2 (Shimadzu, Kyoto Japan).

FIG. 1 shows a scan after running the gel loaded with molecular weight markers, stained with coomassie-brilliant blue. The standards corresponding with peak 1–6, have molecular weights of 78000, 66000, 45000, 30000, 17200 and 12300 D, respectively (LKB 1860-12 Bromma, Sweden).

Figure 2:
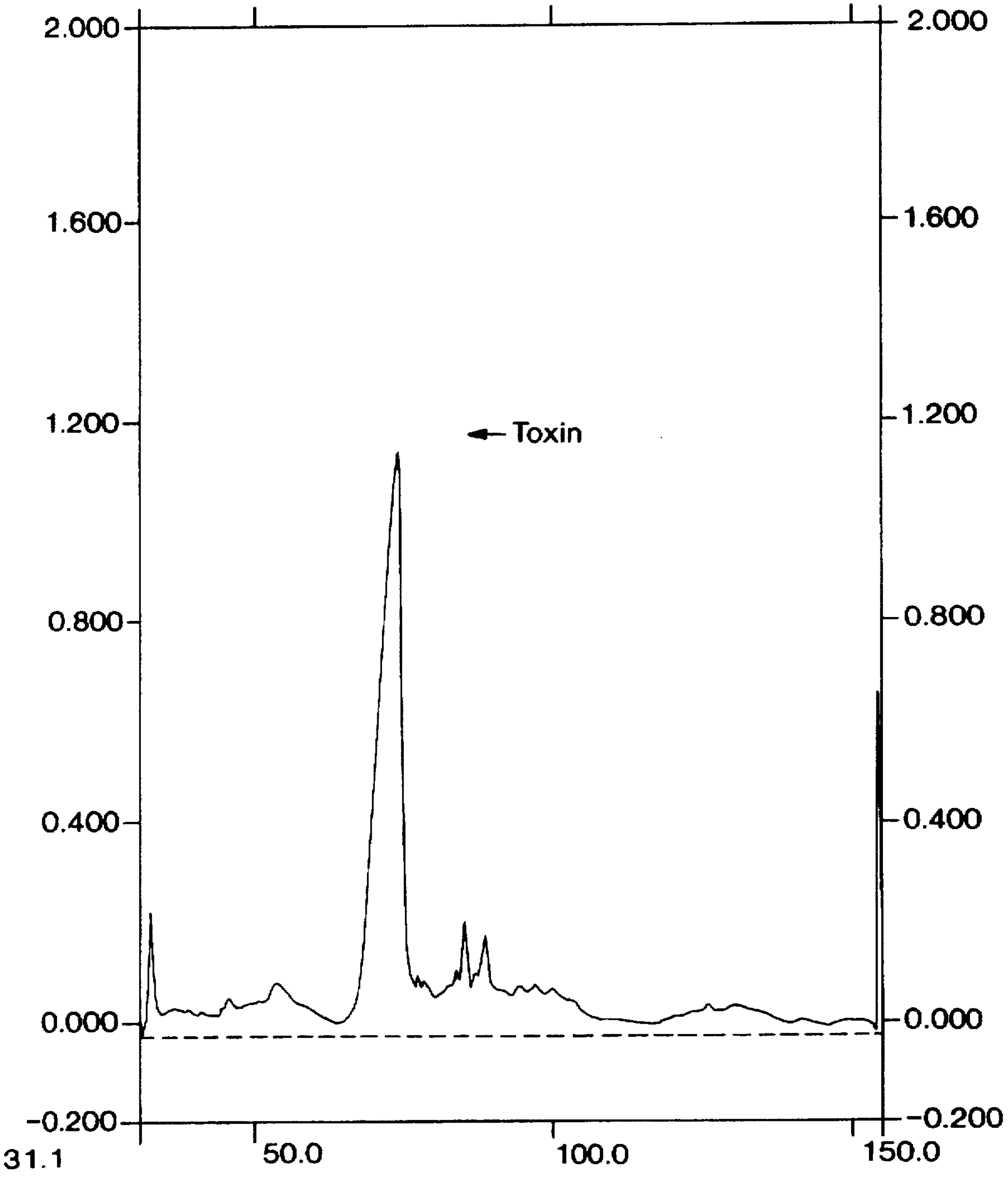
Figure 3:
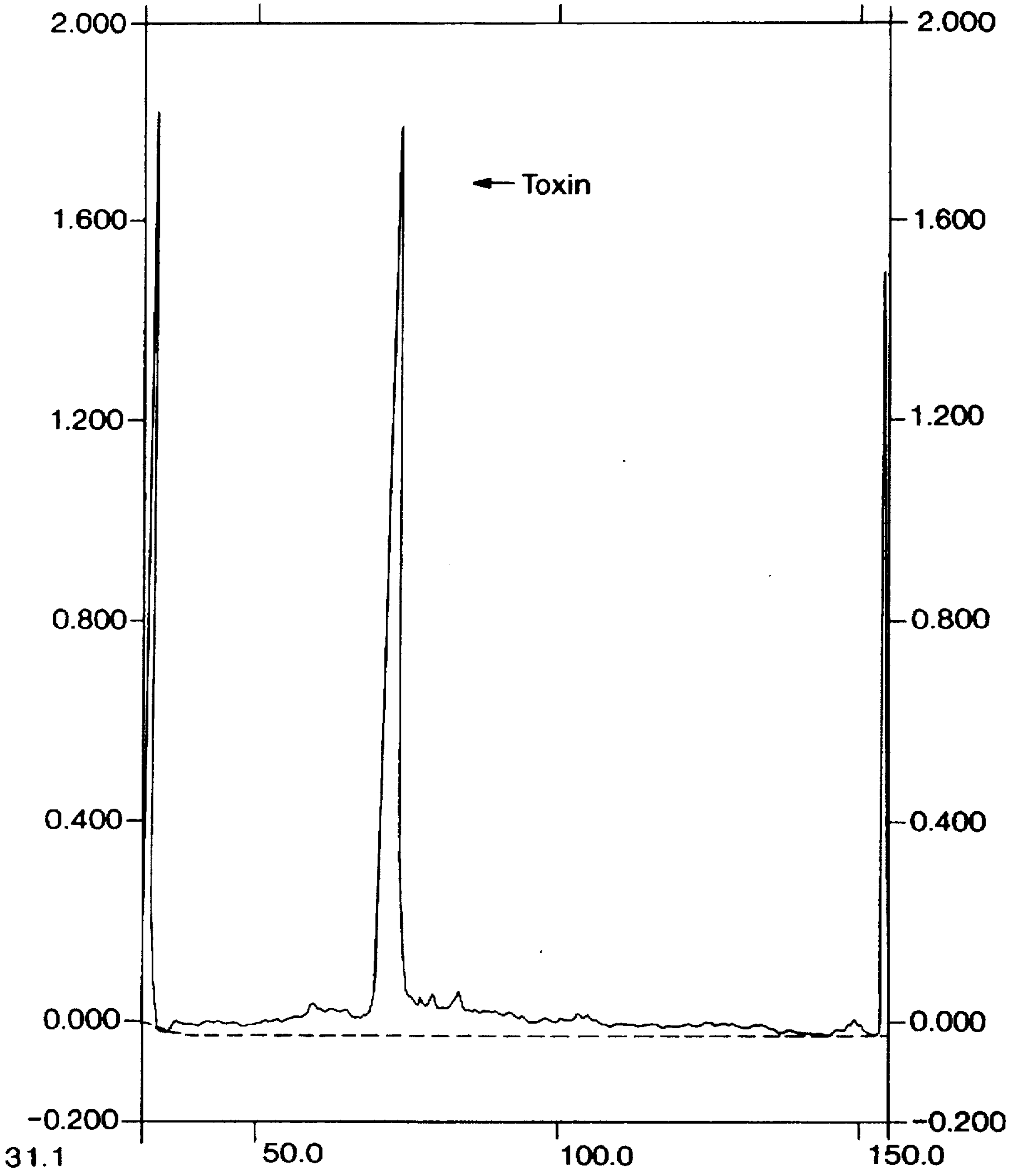

In FIGS. 2 and 3 are represented the scans of the products obtained from step A and step B of Example 1, respectively.

The molecular weight of the toxin subunit of *E. coli* strain CH7 was found in these experiments to be about 47 kD.

E. Iso-electric Point Determination

The iso-electric point of the toxin was determined focussing 3 ml toxin of *E. coli* strain CH7 obtained from step A of Example 1 together with a mixture of 0.5 ml Servalytes pH 3–7 (analytical grade Serva Heidelberg Germany) and 46.5 ml aqua dest for 5 hours at 12 W Rotofor, Bio-Rad Richmond USA). Toxin content was detected by analytical gel electrophoresis.

The results of this experiment are summarized in table 5.

It was found from these results that the toxin of the *E. coli* strain CH7 has an iso-electric point at about pH 4.8.

Results

TABLE 5 pH and toxin values after focussing of 3 ml seph 4B-Cl sample.

| Fraction | pH | Toxin* | Fraction | pH | Toxin* |
|---|---|---|---|---|---|
| 1 | 2.68 | + | 11 | 5.50 | — |
| 2 | 3.26 | ± | 12 | 5.82 | — |
| 3 | 3.50 | – | 13 | 6.23 | — |
| 4 | 3.73 | – | 14 | 6.57 | — |
| 5 | 4.18 | – | 15 | 6.85 | — |
| 6 | 4.38 | ± | 16 | 7.14 | — |
| 7 | 4.55 | ++ | 17 | 7.47 | — |
| 8 | 4.80 | ++++ | 18 | 7.97 | — |
| 9 | 5.09 | ++ | 19 | 8.41 | — |
| 10 | 5.32 | + | 20 | 8.75 | — |

* – = no toxin visible
± = just visible
+ = visible
++, +++, ++++ = increasing amounts of toxin F. Saccharide Contents The toxin of *E. coli* strain CH7 obtained from step B. of Example 1 did neither contain polysaccharide nor any sugars as determined in the phenol-sulphuric acid assay of Dubois et al. (Analytical Chemistry 28, 350–356; 1956). In the Limulus Amoebocyte Lysate test (Pyrotell, Mass., USA) no significant LPS (endotoxin) activity was detected.

G. Amino Acid Analysis

The N-terminal amino acid sequence was determined by the liquid phase DABITC procedure according to Chang (Methods Enzymology 91, 455–466; 1983). Identification of DABTH-amino acids was performed by thin-layer chromatography. The amino acid composition was determined by the PTC technique as described by Janssen et al. (Chromatographia 22, 345–358; 1986), with the assumption that the subunit molecular weight of 47 kD for CH7-FT corresponds with a total of 446 amino acids.

Results

The toxin of *E. coli* strain CH7 obtained from step A and step B of Example 1 had the following N-terminal amino acid sequence:

Ala-Gln-Val-Ile-Asn-Thr-Asn-Ser-Leu-Ser-Leu-(?)-Thr-Gln

This sequence is identical to the N-terminal amino acid sequence of *E. coli* K-12 flagellin as described by Kuwajima et al. (Journal of Bacteriology 168, 1479–1483; 1986).

The amino acid composition of the toxin is given in Table 6 and also shows homology with *E. coli* K-12 flagellin to a considerable degree.

TABLE 6

Estimation of the amino acid composition of CH7-FT and comparison with the amino acid composition of *E. coli* K-12 flagellin: number of amino acids per subunit (percentage).

| Amino acid | CH7-FT[1)] | *E. coli* K-12 flagellin[2)] |
|---|---|---|
| Ala | 50(11.2) | 59(11.9) |
| Arg | 12(2.7) | 11(2.2) |
| Asn } Asp | 52(11.7) | 48 } 39 (17.5) |
| Cys | 4(0.9) | 0(0) |
| Gln } Glu | 43(9.6) | 27 } 14 (6.2) |
| Gly | 37(8.3) | 44(8.9) |
| His | 0(0) | 0(0) |
| Ile | 24(5.4) | 28(5.6) |
| Leu | 32(7.2) | 37(7.4) |
| Lys | 28(6.3) | 25(5.0) |
| Met | 2(0.4) | 3(0.6) |
| Phe | 9(2.0) | 5(1.0) |
| Pro | 8(1.7) | 6(1.2) |
| Ser | 58(13.0) | 43(8.7) |
| Thr | 48(10.8) | 65(13.1) |
| Trp | 0(0) | 0(0) |
| Tyr | 11(2.5) | 10(2.0) |
| Val | 28(6.3) | 33(6.6) |
| Total | 446 | 497 |

1)Estimated by the PTC technique (Chromatographia 22, 345–358; 1986).
2)Calculated on the basis of the DNA sequence (Journal of Bacteriology 168, 1479–1483; 1986).

EXAMPLE 3

Screening of chicken *E. coli* Strains for FT Expression and Serological Characterization of FT A total of 124 chicken *E. coli* isolates from all over the world were screened for their toxicity, motility and expression of FT antigen on the bacterial surface. Polyclonal and monoclonal antibodies were used to visualize the FT and to investigate cross-reactions.

Methods

Toxicity Testing and Toxin Neutralization

The strains were tested for toxicity on Vero cells as described in Example 2B. For neutralization, toxin preparations were incubated with antiserum dilutions for 2 h at 37° C. prior to toxicity testing.

Motility Testing

Motility of the strains was tested in U-shape tubes containing nutrient broth with low (0.25%) agar concentration. These U-tubes were inoculated with an *E. coli* strain at one side, and migration to the other end of the tube was recorded after overnight incubation at 37° C.

Antisera Production

Antisera were raised in rabbits and chickens against the FT of *E. coli* strain CH7 prepared as described in Example 1A. The toxins of strains CH5 and CH7 prepared as described in Example 1B were used for the production of monoclonal antibodies (MoAb). For MoAb production spleen cells from immunized mice were fused with myeloma cells and the resulting hybridomas were screened for antitoxin antibody secretion in an ELISA. Positive hybridomas were cloned by limiting dilution. Ascitic fluid was prepared by intraperitoneal injection of cloned hybridomas into mice. Ascites was inactivated at 56° C. for 10 min., lipids were extracted with 1,1,2-trichlorotrifluoroethane (Merck), and MoAbs were precipitated with 50% saturated ammonium sulphate.

FT Antigen Expression by *E. coli* Strains

Rabbit antiserum raised against the FT of strain CH7 (015:K14:H10) was absorbed for 24 h at room temperature with the non-toxigenic *E. coli* strain RDEC-1 (015:K14). This absorbed antiserum was used to screen strains for FT expression in a whole bacteria ELISA carried out as follows.

Bacteria were grown for 6 hours in TSB without agitation, spun down at 3,000 rpm for 15 min. (Sorvall RT6000) and resuspended in CBB buffer (1.59 g/l $Na_2CO_3$; 2.93 g/l $NaHCO_3$; 0.2 g/l $NaN_3$; pH 9.6) to an O.D. at 660 nm of 0.140–0.180. Flatbottom polystyrene microtiterplates (Greiner) were seeded with 100 µl per well of these bacterial suspensions and allowed to dry up at 50° C. overnight. The plates were washed with tap water and blocked for 1 h. at room temperature with 110 µl per well of PBS-T-N (0.04M PBS; pH 7.2; 0.5% Tween 80; 15% Newborn Calf Serum). Subsequently 100 µl per well of serial dilutions of absorbed serum were added, diluted in PBS-T-N and starting with a 1:100 dilution. Two wells per strain with PBS-T-N served as background controls. After 1 h. incubation at 37° C., the plates were washed and 100 µl per well of peroxidase-conjugated goat-anti-rabbit IgG(H+L) was added to each well in the appropriate dilution in PBS-T-N. After incubation at 37° C. for 30 min. the plates were washed again. Antibody binding was detected calorimetrically by adding 100 µl per well of TMB-substrate buffer, containing ureum-peroxide (Organon Teknika, Oss) and 3,3',5,5'-tetramethylbenzidine in sodium acetate-citric acid buffer (pH 5.5). The reaction was developed in the dark for 10 min., stopped by adding 50 µl 4N $H_2SO_4$, and measured in a Microelisa reader at 450 nm. Titers were determined as the highest antiserum dilution giving an $A_{450}$ of at least 2 times the background $A_{450}$.

In each assay strains CH7 and RDEC-1 were included as positive and negative controls respectively.

Western Blotting

Immunoblotting or Western blotting was performed essentially as described by Muilerman et al. (Anal. Biochem. 120, 46–51; 1982). Crude FT preparations of strains were prepared by growing bacteria in Trypticase Soy Broth for 6 h with agitation. Bacteria were removed by centrifugation after vigorous mixing, and supernatant was concentrated approx. 40 times by ethanol precipitation (1 part supernatant with 2 parts 96% ethanol, overnight incubation at 4° C., centrifugation and dissolving the precipitate in 0.04 mol/l PBS, pH 7.2). These crude FT preparations were run in SDS-PAGE and transblotted to cellulose nitrate membrane filter. Antigens were visualized by the successive incubation with antibodies, appropriate peroxidase-conjugated anti-species IgG (H+L), and ureum peroxide with 3,3'-diaminobenzidine. 4HCl.

Immunogold-Electronmicroscopy (IG-EM)

IG-EM was carried out essentially as described by van Alphen et al. (Infect. Immun. 56, 1800–6; 1988). Briefly, bacteria grown in Trypticase Soy Broth were incubated with antibody dilutions in PBS plus 1% BSA plus 0.05% Tween 20 (PBS-B-T), washed thrice with PBS and incubated with protein A labeled with gold spheres in PBS-B-T. After three more washings with PBS bacteria were transferred to Formvar-coated grids and negatively stained with 1% uranyl acetate or phosphotungstic acid.

Results

In a collection of 124 chicken *E. coli* strains from all over the world, 73 strains (59%) excreted detectable amounts of toxin active on Vero cells. A further 37 strains (30%) were toxic for Vero cells after lysis of the bacteria. In whole bacteria ELISA 52 strains (42%) reacted with antiserum raised against CH7-FT. All strains that were positive in the ELISA also produced extracellular Vero toxin (Table 7).

TABLE 7

Relation between Vero toxicity and reactivity with antiserum raised against CH7-FT (numbers of strains)

| | | Vero toxicity[2)] | |
|---|---|---|---|
| | | + | – |
| anti CH7-FT reactivity[1)] | + | 52 | 0 |
| | – | 21 | 51 |

[1)]Reaction in whole bacteria Elisa with CH7-FT antiserum
[2)]Toxicity for Vero cells of bacterial culture supernatant.

A strong correlation was found between Vero toxin excretion and motility of the strains (Table 8).

TABLE 8

Relation between Vero toxicity and motility (numbers of strains)

| | | Vero toxicity[2)] | |
|---|---|---|---|
| | | + | – |
| Motility[1)] | + | 69 | 10 |
| | – | 4 | 41 |

[1)]Motility in U-tubes
[2)]Toxicity for Vero cells of bacterial culture supernatant.

These results provide additional evidence that the Vero toxic activity resides in the flagella. It was also found that Vero toxicity increased after passage of bacteria through U-tubes. Furthermore, these results show that the toxins of different strains are serologically cross reactive.

The cross reaction between the toxins of different strains was further investigated. In Table 9 it is shown that both rabbit and chicken antisera raised against FT of strain CH7 neutralized the Vero toxicity of all other toxigenic strains tested. MoAbs raised against FT of strains CH5 and CH7 did not neutralize toxicity at all.

TABLE 9

Neutralization of Vero toxicity in culture supernatant by antisera raised against CH7-FT

| | | Vero toxin titer[1)] | | |
|---|---|---|---|---|
| Strain | Serotype | Control[2)] | K07577[3)] (1:10) | BB1-2[4)] (1:10) |
| CH3 | O45:K—:H9 | 8 | — | — |
| CH5 | O2:K1:H5 | 16 | — | — |
| CH7 | O15:K14:H10 | 32 | — | — |
| CH125 | O1:K1:H7 | 32 | 4 | — |
| CH135 | O2:K1:H4 | 64 | 4 | — |

[1)]see Table 2.
[2)]Sham-treated supernatant, or treated with pre-immune serum.
[3)]Rabbit anti CH7-FT antiserum, 1:10 diluted.
[4)]Chicken anti CH7-FT antiserum, 1:10 diluted.

TABLE 10

Western blotting of crude FT preparations from various strains with antisera, and comparison with corresponding flagellin molecular weight.

| | | Antibodies[1] | | | | | Flagellin |
|---|---|---|---|---|---|---|---|
| Strain | Serotype | KO7577 | BB1-2 | αH10 | Int 1-7 | Int 12-13 | MW |
| CH3 | O45:K—:H9 | 70[2] | 70 | 70 | — | 70 | 69[3] |
| CH5 | O2:K1:H5 | 43 | 43 | 43 | — | 43 | 46[3] |
| CH7 | O15:K14:H10 | 47 | 47 | 47 | 47 | 47 | 45–47[4] |
| CH125 | O1:K1:H7 | 60 | 60 | 60 | — | 60 | 61[3] |
| CH135 | O2:K1:H4 | 35 | 35 | 35 | — | 35 | 37[3] |

[1]KO7577 = rabbit antiserum raised against CH7-FT; BB1-2 = chicken antiserum raised against CH7-FT; αH10 = agglutinating antiserum for H10 flagella typing, purchased from RIVM (Bilthoven); Int1-7 = MoAb raised against CH7-FT; Int12-13 = MoAb raised against CH5-FT.
[2]Data represent approx. apparent MW of single or major bands in blot in kD.
[3]A. M. Lawn (J. Gen. Microbiol. 101, 112–130; 1977).
[4]Own observation with H10 flagella reference strains.

The results of Western blotting of crude FT preparations with various antisera are shown in Table 10. Rabbit and chicken antisera raised against CH7-FT (KO7577 and BB1-2, respectively) reacted with all other FT preparations tested, although the MW of the bands differed among strains. Identical results were obtained using an anti-H10-flagella agglutinating antiserum. Also MoAb Int12-13, raised against CH5-FT showed an identical pattern in Western blotting. MoAb Int1-7, raised against CH7-FT, only reacted with the 47 kD band of CH7-FT. Strikingly, the flagellin MWs corresponding with the H types of the various strains were almost identical with the apparent MWs of the respective FTs. A number of strains with H10 type flagella, obtained from RIVM (Bilthoven), showed bands at either 45 kD or 47 kD in Western blotting with the polyclonal antisera. MoAb Int1-7 only reacted with the 47 kD band of H10 flagella strains. The intensity of the bands in Western blotting was increased when strains were passed through U-tubes prior to preparing crude FT.

In IG-EM, flagella-like filaments on both CH5 and CH7 bacteria were labeled with gold spheres, using polyclonal antisera raised against CH7-FT. With MoAb Int1-7, raised against CH7-FT, only flagella-like filaments on CH7 and not on CH5 bacteria were labeled with gold spheres. With MoAb Int12-13, raised against CH5-FT prepared as described in Example 1B using preparative SDS-PAGE, flagella-like filaments were not labeled significantly; only some gold spheres were observed on CH5 and CH7 bacterial surfaces. In fact, MoAb Int12-13 only reacted with dissociated FT (Western blot, ELISA) and not with intact FT (IG-EM, ELISA).

All these results point out that the Vero toxic activity resides in the flagella, or that FT is identical to flagella. Furthermore, the FTs of different strains are serologically highly cross-reactive and also cross-neutralizing.

EXAMPLE 4

Protection of Broilers by Passive Immunization

Antiserum was raised against CH7-FT by vaccinating chickens with CH7-FT prepared as described in Example 1A. Antisera from different chickens were pooled and inactivated at 56° C. for 10 min.

Three-week old broilers (Euribrid, Boxmeer, The Netherlands) were injected intravenously with 1 ml of this CH7-FT antiserum. Within 1 hour after antiserum injection the chickens were infected by injection of 0.2 ml of bacterial suspension into the right posterior thoracic air sac. Bacteria were cultured overnight on blood agar base plates (Oxoid), suspended in PBS and diluted to the appropriate concentration. The *E. coli* strains used were all isolated from affected hearts of chickens with colibacillosis. Control chickens, to which no antiserum was administered or only negative control serum, were infected with the same doses of bacteria. After challenge the chickens were housed in reduced-pressure isolators with food and water ad lib. Mortality was scored for 7 days after challenge.

As shown in Table 11, passive immunization of chickens with CH7-FT antiserum afforded significant protection against challenge with 3 out of 5 *E. coli* strains tested. Of these 3 strains against which significant protection was seen, 2 strains excreted toxic activity in the culture supernatant and one strain had toxic activity for Vero cells only in bacterial lysate. The 2 strains against which no significant protection was seen both had toxic activity only in bacterial lysate. Strikingly, significant protection was only obtained against challenge with motile strains.

TABLE 11

Protection of broilers against *E. coli* infection by passive immunization with CH7-FT antiserum.

| No. | Serotype | Toxin[1] | Motile[2] | Dose | CH7-FT antiserum administered | Mortality[3] (number out of total) | P < 0.05[4] |
|---|---|---|---|---|---|---|---|
| CH2 | O78:K80:H4 | lys | + | $5 \times 10^6$ | + | 7/16 | + |
| CH2 | O78:K80:H4 | lys | + | $5 \times 10^6$ | – | 14/16 | |
| CH5 | O2:K1:H5 | sup | + | $10^6$ | + | 3/16 | + |
| CH5 | O2:K1:H5 | sup | + | $10^6$ | – | 6/9 | |
| CH6 | O1:K1:H— | lys | – | $10^7$ | + | 15/33 | – |
| CH6 | O1:K1:H— | lys | – | $10^7$ | – | 21/36 | |
| CH7 | O15:K14:H10 | sup | + | $2 \times 10^6$ | + | 3/32 | + |
| CH7 | O15:K14:H10 | sup | + | $2 \times 10^6$ | – | 18/29 | |
| CH245 | O35:K—:H— | lys | – | $5 \times 10^6$ | + | 6/17 | – |
| CH245 | O35:K—:H— | lys | – | $5 \times 10^6$ | – | 7/19 | |

[1] Toxic activity on Vero cells of culture supernatant (sup) or of bacterial lysate only (lys).
[2] Motility of strains in U-shape tubes.
[3] Number of dead chickens within 7 days after challenge out of total.
[4] Chi-square test for significant protection by antiserum.

I claim:

1. A vaccine for the protection of a bird against infection by *E. coli* having flagellar toxin, comprising an effective amount for protecting a bird against *E. coli* flagellar toxin toxic activity of isolated and purified *E. coli* toxic flagella having flagellin subunits with a molecular weight range of about 37 to about 69 kD found associated in and/or with filamentous aggregates, not naturally possessing bound carbohydrate residues, having immunizing activity against *E. coli* flagellar toxin toxic activity in birds, having toxic activity against Vero cells and day-old chicks, and retaining toxicity on heating for 1 hour at 100° C., and a pharmaceutically acceptable carrier.

2. A vaccine according to claim 1, wherein the toxic activity in the flagella toxin is inactivated.

3. A method for protecting birds against an *E. coli* infection by *E. coli* having flagellar toxin, comprising administering an effective amount for protecting a bird against *E. coli* flagellar toxin toxic activity of a vaccine according to claim 1.

4. A method for the preparation of a vaccine for the protection of a bird against *E. coli* infection comprising, (a) culturing *E. coli* cells having flagella that possess toxic activity against Vero cells, (b) separating the flagella from the *E. coli* cells, and (c) adding to the separated flagella at least one of the following:

i. pharmaceutically acceptable salts,
  ii. an inactivating agent,
  iii. a buffer,
  iv. a pharmaceutically acceptable carrier or diluent,
  v. an adjuvant, or
  vi. an emulsifier.

5. A method for protecting a bird against an *E. coli* infection by *E. coli* having flagellar toxin, comprising administering an effective amount for protecting a bird against *E. coli* flagellar toxin toxic activity of a vaccine according to claim 2.

6. The vaccine for the protection of a bird against an *Escherichia coli* infection by *E. coli* having flagellar toxin of claim 1, wherein the flagella have flagellin subunits with a molecular weight of about 47 kD as measured by SDS-PAGE.

7. A method for protecting a bird against an *E. coli* infection by *E. coli* having flagellar toxin, comprising administering an effective amount for protecting a bird against *E. coli* flagellar toxin toxic activity of a vaccine according to claim 6.

* * * * *